United States Patent
Fatutto et al.

(10) Patent No.: US 6,180,841 B1
(45) Date of Patent: *Jan. 30, 2001

(54) SINGLE STAGE FIXED BED OXYCHLORINATION OF ETHYLENE

(75) Inventors: Pierluigi Fatutto, Mestre; Andrea Marsella, Paese; Dario Vio, Marghera, all of (IT)

(73) Assignee: EVC Technology AG (CH)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/817,415

(22) PCT Filed: Sep. 27, 1995

(86) PCT No.: PCT/IB95/00872

§ 371 Date: Apr. 18, 1997

§ 102(e) Date: Apr. 18, 1997

(87) PCT Pub. No.: WO96/12693

PCT Pub. Date: May 2, 1996

(30) Foreign Application Priority Data

Oct. 20, 1994 (GB) .................................... 9421136

(51) Int. Cl.[7] .................................. C07C 17/15
(52) U.S. Cl. ............................ 570/224; 570/225
(58) Field of Search ...................... 570/224, 225

(56) References Cited

U.S. PATENT DOCUMENTS

| | | | |
|---|---|---|---|
| 3,042,728 | * 7/1962 | Hirsh et al. | 570/245 |
| 3,184,515 | 5/1965 | Penner et al. | 260/658 |
| 3,475,505 | 10/1969 | Hornig et al. | 260/659 |
| 3,551,506 | 12/1970 | Weinstein | 260/656 |
| 3,629,354 | 12/1971 | Beard, Jr. | 260/683.3 |
| 3,699,178 | 10/1972 | Suzuki et al. | 260/659 A |
| 3,879,481 | 4/1975 | Sze et al. | 267/656 R |
| 3,892,816 | * 7/1975 | Kister | 570/245 |
| 3,937,744 | 2/1976 | Riegel | 260/656 R |
| 3,987,118 | 10/1976 | Kuck | 260/654 A |
| 3,992,463 | 11/1976 | Benaroya et al. | 260/659 A |
| 4,100,211 | 7/1978 | Magistro | 260/656 R |
| 4,123,467 | 10/1978 | Campbell et al. | |
| 4,124,534 | 11/1978 | Leitert et al. | 252/441 |
| 4,300,005 | 11/1981 | Li | 570/224 |
| 4,451,683 | 5/1984 | Davies et al. | 570/224 |
| 4,467,127 | 8/1984 | Kroenke et al. | 570/224 |
| 5,097,083 | 3/1992 | Stauffer | 570/241 |
| 5,113,027 | 5/1992 | Mainz et al. | 570/224 |
| 5,260,247 | 11/1993 | Helmut et al. | 502/225 |
| 5,663,465 | 9/1997 | Clegg et al. | 570/224 |

FOREIGN PATENT DOCUMENTS

| | | |
|---|---|---|
| 704463 | 2/1965 | (CA) . |
| 2540067 | 4/1976 | (DE) . |
| 3226028 | 2/1983 | (DE) . |
| 0146925 A2 | 7/1985 | (EP) . |
| 1355870 | 2/1964 | (FR) . |
| 2067305 | 8/1971 | (FR) . |
| 2210593 | 7/1974 | (FR) . |
| 2285359 | 4/1976 | (FR) . |
| 894138 | 4/1962 | (GB) . |
| 996323 | 6/1965 | (GB) . |
| 1039369 | 8/1966 | (GB) . |
| 1256245 | 12/1971 | (GB) . |
| 1460688 | 1/1977 | (GB) . |
| 1492945 | 11/1977 | (GB) . |
| 2009164 | 6/1979 | (GB) . |
| 2101596 | 1/1983 | (GB) . |
| 51-056404 | 5/1976 | (JP) . |
| 7510050 | 3/1976 | (NL) . |
| 567714 | 12/1977 | (SU) . |
| WO 95/07249 | 3/1995 | (WO) . |
| WO 95/07250 | 3/1995 | (WO) . |
| WO 95/07251 | 3/1995 | (WO) . |

* cited by examiner

*Primary Examiner*—Alan Siegel
(74) *Attorney, Agent, or Firm*—Woodcock Washburn Kurtz Mackiewicz & Norris LLP

(57) ABSTRACT

A method for the oxychlorination of ethylene to produce 1,2-dichloroethane comprises reacting ethylene with a chlorine source and an oxygen source in a fixed-bed oxychlorination reactor in the presence of a catalyst, and is characterized in that a single reactor is used and ethylene is present in a large molar excess with respect to chlorine. The chlorine source is suitably HCl, the catalyst is suitably a cupric chloride catalyst, and the molar excess of ethylene is preferably between 200 and 700%.

10 Claims, No Drawings

SINGLE STAGE FIXED BED OXYCHLORINATION OF ETHYLENE

This application is a 371 of PCT/IB95/00872 filed Sep. 27, 1995.

The present invention relates to the oxychlorination of ethylene in a fixed bed reactor system which consists of a single reactor, to produce chlorinated hydrocarbons, particularly 1,2-dichloroethane (EDC).

It is well known that hydrocarbons such as ethylene may be chlorinated by reacting them with hydrogen chloride and gases containing elemental oxygen, particularly air or oxygen enriched air, in the presence of a catalyst at elevated temperatures and pressures in order to produce chlorinated hydrocarbons such as EDC. The reaction may be carried out with two different reactor technologies. The first is fluid bed reactor technology wherein a gaseous mixture of reactants is contacted with a fluidizable catalyst powder. The second is fixed bed reactor technology, in which the gaseous reactants flow over a fixed catalyst inside the reactor.

Fluid bed reactors have a number of drawbacks, such as potential stickiness of the catalyst powder, unsteady operation, poor selectivity owing to the gas and catalyst solids back mixing in the reactor, loss of heat transfer owing to fouling of the cooler bundle and limits in reagent velocity imposed by the need to avoid catalyst loss by elutriation from the reactor.

Fixed bed reactor technology has been developed in order to overcome these problems (see U.S. Pat. Nos. 3,892,816 and 4,123,467).

Although the fixed bed reactor overcomes many of the problems incurred with the fluid bed reactor system, a number of new problems have been encountered. A major problem is the difficulty, in the fixed bed reactor, of transferring the heat developed by the exothermic oxychlorination reaction away from the reactor to prevent overheating. For this reason, all the necessary reagents may not be fed in the correct stoichiomentric ratio to the reactor. Moreover, because it can be unsafe to have an oxygen concentration of above 8% in the mixture feeding the reactor, for flammability reasons, the reaction is carried out in two or more subsequent stages (usually three) such that the ethylene is introduced into the first reactor while the HCl and oxygen feeds are split between the reactors. Unreacted ethylene plus some inert gases are recycled back to the first reactor.

In a further attempt to reduce the incidence of hot spots and the like, it is known to alter the activity profile of the catalyst within a fixed bed reactor such that the activity increases in the direction of flow. For example, see European patent application 0146925. However, in the prior art, even when a profiled catalyst is used it has been deemed necessary to use a multi-reactor system.

We have now developed a new process for the catalytic oxychlorination of ethylene which makes use of a single fixed-bed reactor. Nevertheless, hot-spots are avoided and good selectivity to ethylene is achieved, as well as over 99% utilisation of HCl.

According to a first aspect of the invention, we provide a method for the oxychlorination of ethylene to produce 1,2-dichloroethane (EDC), comprising reacting ethylene, a chlorine source and an oxygen source in a fixed-bed oxychlorination reactor in the presence of a catalyst, characterised in that a single reactor is used and ethylene is present in a large molar excess with respect to chlorine.

Preferably, the chlorine source is HCl.

Preferably, the ethylene is introduced in a 200–700% molar equivalent excess with respect to stoichiometric HCl, in order to produce a high partial pressure of ethylene.

The oxygen source may be pure oxygen, or an oxygen-enriched gas. Oxygen is preferably supplied in a molar excess of up to 15%, more preferably between 2 and 8%, with respect to HCl.

The large excess of ethylene present functions to increase the selectivity of the reaction, as well as acting as a heat sink, exploiting its high specific heat capacity. Unreacted ethylene is preferably recovered and recycled back to the reactor, or to other processes requiring ethylene such as in direct chlorination reactions.

The composition of the recycle gas reaches an equilibrium depending mainly on combustion rate, the amount of inert gases in the raw materials and the purge rate. Depending on these factors, ethylene concentration can vary between 10 and 90%. As a consequence, the actual ethylene excess used will depend on its concentration in the recycled vent gas and on the recycle flow rate.

In general, the ethylene excess with respect to its stoichiometric requirement as determined by the amount of HCl can be expressed as a percentage calculated according to the formula:

$$200 \frac{(Q1 + Q2 - Q6)}{Q3}$$

where 100 is the stoichiometirc requirement, and wherein $$Q2 = Q4Q1 - 1/2\, Q3 - Q5 - \frac{Q6}{Q1 - 1/2\, Q3 + Q5}$$

and $$Q4 = \frac{100 Q7 - Q8\%\ O_2\ \text{in}}{\%O_2\ \text{in} - \%O_2\ rec}$$

where

% $O_2$ in—oxygen at inlet of reactor

% $O_2$ rec=oxygen in recycle stream.

The symbols are defined as follows:

Q1=mol/h fresh ethylene
Q2=mol/h recycled ethylene
Q3=mol/h HCl
Q4=mol/h total recycle
Q5=mol/h burned ethylene
Q6=mol/h fed inert gases
Q7=mol/h fed oxygen
Q8=mol/h total fresh reagents Control of the recycled gas flow rate may be used to adjust the oxygen concentration at the inlet of the reactor and thereby the hotspot temperature. In the conditions of temperature and pressure existing in the inlet of the reactor, the lower flammability limit of the mixture occurs when the oxygen concentration is around 8%. For safety and operational reasons, the concentration is advantageously between 5 and 6% v/v, as use of a higher concentration can result in an elevated hotspot temperature in the catalytic bed.

Typically, the hotspot temperature would be about 230–280° C., depending on a number of factors, including reactor diameter.

The reactor employed in the method of the invention is a tubular reactor. Advantageously, it consists of a plurality of tubes stacked together within a single coolant jacket. The internal diameter of each tube is preferably between 20 and 40 millimeters. Diameters of less than 20 millimeters are disadvantageous as an excessive number of tubes is required in an industrial reactor in order to obtain a satisfactory throughput of materials, while diameters larger than 40 millimeters result in excessively high hotspot temperatures inside the catalytic bed.

The preferred length of the reactor is between 3.5 and 8 meters. A length of less than 3.5 meters results in too short a residence time and therefore either low reactant conversion or low specific throughput; a length of more than 8 meters is not necessary in order to achieve both high HCL and oxygen conversion and large specific throughput.

Catalyst layers within the reactor can be arranged in a number of ways. For example, the reactor may simply be filled with catalyst in the normal manner, not employing a profiled catalyst distribution. Alternatively, a simple loading pattern maybe employed whereby the catalyst is loaded in two layers, a first of low activity catalyst or diluted catalyst (See U.S. Pat. No. 4,123,467) in order to avoid hotspots and a second of a more active or more concentrated catalyst, in order to increase the rate of reaction. A further, more complex loading pattern consists of a succession of several layers of catalyst with increasing activity (or concentration) from the first to the last layer. The choice of suitable catalyst loading pattern will depend on the maximum temperature of the hotspot, as well as the inside diameter and length of the tubular reactor and on the projected throughput.

Invariably, it is advantageous to fill the last part of the reactor with a high activity catalyst as used in the third reactor of a three stage oxychlorination process.

Catalysts for use in the invention are known in the art and are supported catalysts in which cupric chloride is the major active component and alumina, silica gel, alumino-silicate and the like form the supports. The support material may be present in the form of spheres, cubes, cones, hollow cylinders, cylindrical pellets, multilobate pellets and other shapes.

In addition to cupric chloride, the catalyst may also comprise promoters such as potassium, magnesium, sodium, lithium, calcium, cerium and cesium chlorides for improving the selectivity to EDC. The activity prolfile of the catalyst in the catalytic bed would be arranged in such a way as to have the HCl conversion above 98% at a point 70 to 80% of the distance along the catalytic bed. The last 20 to 30% of the catalytic bed will perform as a finisher, so that the whole reaction is assured of a high conversion even if the first part of the catalytic bed loses activity over time.

Preferably, the reactants are preheated to between 100 and 200° C. The reaction pressure can range up to 20 barg, the preferred range being between 4 and 7 barg.

The invention will now be described, for the purposes of exemplification only, in the following examples with reference to the appended figure, which is a systematic diagram of a single reactor oxychlorination apparatus.

EXAMPLE 1

The reactor is a unit composed of 1 inch external diameter (e.d) nickel tube 14 BWG 25 feet long; inside on the axis there is a thermowell of 6 mm e.d. containing 8 thermocouples with which it is possible to record the thermal profile of the reactor. The reactor is surrounded with an external jacket in which steam at 210° C. and 18 barg is used to control the temperature of the reaction. The reactor pressure is controlled with a pneumatic valve on an effluent line.

The reagents were preheated in 18 barg steam heated exchangers; subsequently, ethylene, HCl and nitrogen were mixed together and oxygen was added in a mixer where the velocity of the gases is higher than the speed of ethylene flame propagation. The catalyst used was a normal industrial catalyst for oxygen three stage fixed bed process consisting of hollow cylinders containing copper and potassium chloride arranged such that the amount of the copper varies from 24 to 60 gr/liter from inlet to outlet of the reactor. The catalytic bed was 2.6 liters. In this reactor, a mixture of 2–3.1 moles/h of ethylene, 66.8 moles/h of HCl, 17.5 moles/h of oxygen and 18 moles/h of nitrogen was introduced. The oxygen excess was 4.8%.

Nitrogen was used to stimulate the inert gases of the recycle gas and its amount was a function of the recycle ratio. In this case the recycle composition was 90% ethylene and 10% inert gases. The pressure at inlet was 5.1 barg and at outlet 3.5 barg. The temperature of cooling jacket was held at 210° C. The outlet stream, consisting of a mixture of ethylene, oxygen, HCl, nitrogen, EDC, water, COx and byproducts, was analyzed and the results were:

| | |
|---|---|
| Oxygen conversion to crude EDC | 94.7% |
| HCl conversion to crude EDC | 99.4% |
| EDC production | 32.8 mol/h. |
| Selectivity of ethylene to COx | 0.6% mol |
| Selectivity of ethylene to ECl | 0.24% mol |
| Selectivity of ethylene to EDC | 98,66% mol |
| Selectivity of ethylene to chloral | 0,15% mol |
| Selectivity of ethylene to impurities | 0,35% mol |
| Hotspot | 233° C. |

EXAMPLE 2

This example was carried out with the same reactor and catalytic scheme as in example 1. It was fed a mixture of 30 ethylene 169 moles/h, HCl 71.5 moles/h, oxygen 19.5 moles/h and nitrogen 65 moles/h. The oxygen excess was 9%. Recycle composition was ethylene 70%, inerts 30% v/v. The outlet pressure was 7.2 barg. The cooling jacket temperature was 210° C. The results were:

| | |
|---|---|
| Oxygen conversion to crude EDC | 90.8% |
| HCl conversion to crude EDC | 99.5% |
| EDC production | 35.6 moles/h |
| Selectivity of ethylene to COx | 0,34% mol |
| Selectivity of ethylene to ECl | 0,17% mol |
| Selectivity of ethylene to chloral | 0,20% mol |
| Selectivity of ethylene to EDC | 98,92% mol |
| Selectivity of ethylene to impurities | 0.37% mol |
| Hotspot | 277° C. |

EXAMPLE 3

This example was carried out with the same reactor and catalytic scheme of examples 1 and 2. It was a fed a mixture of ethylene 267.55 moles/h, HCl 93.45 moles/h, oxygen 25 moles/h, nitrogen 50moles/h. Oxygen excess was 7%. Recycle composition: ethylene 80%, inerts 20% v/v. Outlet pressure was 3.2 barg and the inlet pressure 6.6 barg. The cooling jacket temperature was 210 C. The results were:

| | |
|---|---|
| Oxygen conversion to crude EDC | 90.9% |
| HCl conversion to crude EDC | 99% |
| EDC production | 46.2 moles/h |
| Selectivity of ethylene to COx | 0.13% mol |
| Selectivity of ethylene to ECl | 0,25% mol |
| Selectivity of ethylene to chloral | 0,10% mol |

| | |
|---|---|
| Selectivity of ethylene to EDC | 99,12% mol |
| Selectivity of ethylene to impurities | 0,40% mol |
| Hotspot | 233° C. |

EXAMPLE 4

A reactor consisting of one 1.25 inch e.d. nickel tube 14 BWG 12 feet long was set up, the same as that used in a normal three stage industrial reactor, inside of which there was a thermowell of 6 mm e.d. containing 4 sliding thermocouples. The temperature, pressure control and reagent feeding systems were as in Example 1. The catalytic bed was 1.8 liters. The catalyst used was the same type as in other examples. The copper content ranged from 24 to 46 gr/liter.

It was fed a mixture of 272 moles/h of ethylene, HCl 97.5 moles/h, oxygen 26.8 moles/h and nitrogen 24.6 moles/h. The oxygen excess was 10%. Recycle composition was 90% ethylene, 10% inerts. The outlet pressure was 5.5 barg and the pressure drop 0.55 barg. The results were:

| | |
|---|---|
| Oxygen conversion to crude EDC | 89% |
| HCl conversion to crude EDC | 98% |
| EDC production | 47.6 moles/h |
| Selectivity of ethylene COx | 0.13% mol |
| Selectivity of ethylene to ECl | 0.20% mol |
| Selectivity of ethylene to EDC | 99.10% mol |
| Selectivity of ethylene to chloral | 0.15% mol |
| Selectivity of ethylene to impurities | 0.42% mol |
| Hotspot | 258° C. |

EXAMPLE 5

The same reactor and catalytic scheme as in Example 4 was fed a mixture of 214.2 moles/h ethylene, 84.7 moles/h of HCl, 24.1 moles/h of oxygen and 21.6 moles/h of nitrogen. Oxygen excess was 13.4%. Recycle composition was 90% ethylene, 10% inerts. The outlet pressure was 5.5 barg and the pressure drop was 0.5 barg. The results were:

| | |
|---|---|
| Oxygen conversion | 87.1% |
| HCl conversion | 99.1% |
| EDC production | 42 moles/h |
| Selectivity of ethylene to COx | 0.30% mol |
| Selectivity of ethylene to ECl | 0.20% mol |
| Selectivity of ethylene to EDC | 98.50% mol |
| Selectivity of ethylene to chloral | 0.20% mol |
| Selectivity of ethylene to impurities | 0.80% mol |
| Hotspot | 270° C. |

EXAMPLE 6

Using the same reactor as in Examples 4 and 5 but with the same loading pattern as in the first stage of a three stage process consisting of a catalyst containing 26 gr/liter of copper and 12 gr/liter of potassium in the first 3/5 of the reactor and 40 gr/liter of copper and 18 gr/liter of potassium in the remainder part, a mixture of ethylene 231 moles/h, oxygen 18 moles/h, HCl 64.8 moles/h and nitrogen 42 moles/h was reacted. The outlet pressure was 5.5 barg and the pressure drop was 0.45 barg.

| | |
|---|---|
| Oxygen conversion to crude EDC | 88.5% |
| HCl conversion to crude EDC | 97.8% |
| EDC production | 31.7% moles/h |
| Selectivity of ethylene to COx | 0.10% mol |
| Selectivity of ethylene to ECl | 0.20% mol |
| Selectivity of ethylene to EDC | 99.30% mol |
| Selectivity of ethylene to chloral | 0.10% mol |
| Selectivity of ethylene impur | 0.30% mol |
| Hotspot | 255° C. |

What is claimed is:

1. A method for the oxychlorination of ethylene to produce 1,2-dichloroethane (EDC), comprising reacting ethylene with a chlorine source and an oxygen source in a fixed-bed oxychlorination reactor in the presence of a catalyst, characterised in that the method is a single stage method where the reactants are fed to the inlet of the reactor, the ethylene is present in a molar excess with respect to chlorine of between 200 and 700%, and the oxygen is present in a molar excess of up to 15 % with respect to the chlorine.

2. A method according to claim 1 wherein the chlorine source is HCl.

3. A method according to claim 1 or claim 2 wherein the catalyst is a cupric chloride catalyst.

4. A method according to claim 3 wherein the catalyst further comprises the chlorides of potassium, magnesium, cesium, sodium, lithium, calcium or cerium.

5. A method according to claim 1 wherein the molar excess of oxygen is between 2 and 8%.

6. A method according to claim 1 wherein the activity profile of the catalyst increases in the direction of reagent flow.

7. A method according to claim 1 wherein the reactor comprises at least one tube having an internal diameter of between 20 and 40 mm, and a length between 3.5 and 8.5 m.

8. A method according to claim 1 wherein vent gases are recycled.

9. A method according to claim 1 wherein vent gases are recycled.

10. A method according to claim 1 wherein the 1,2-dichloroethane is removed from said reactor following said reaction.

* * * * *

UNITED STATES PATENT AND TRADEMARK OFFICE
CERTIFICATE OF CORRECTION

PATENT NO. : 6,180,841 B1
DATED : January 30, 2001
INVENTOR(S) : Fatutto et al.

It is certified that error appears in the above-identified patent and that said Letters Patent is hereby corrected as shown below:

Column 2,
Line 29, the formula should appear as follows:

$$Q2 = Q4 \frac{Q1 - 1/2\,Q3 - Q5 - Q6}{Q1 - 1/2\,Q3 + Q5}$$

Line 38, please delete "% $O_2$ in -- oxygen" and insert -- % $O_2$ in = oxygen -- therefor;

Column 3,
Line 9, please delete "HCL" and insert -- HCl -- therefor;
Line 56, please delete "(e.d)" and insert -- (e.d.) -- therefor;

Column 4,
Lines 5 & 6, please delete "2-3.1 moles/h" and insert -- 223.1 moles/h -- therefor;
Line 23, please delete "98,66% mol" and insert -- 98.66% mol -- therefor;
Line 24, please delete "0,15% mol" and insert -- 0.15% mol -- therefor;
Line 25, please delete "0,35% mol" and insert -- 0.35% mol -- therefor;
Line 32, please delete "30";
Line 43, please delete "0,34% mol" and insert -- 0.34% mol -- therefor;
Line 44, please delete "0,17% mol" and insert -- 0.17% mol -- therefor;
Line 45, please delete "0,20% mol" and insert -- 0.20% mol -- therefor;
Line 46, please delete "98,92% mol" and insert -- 98.92% mol -- therefor;
Line 58, please delete "210 C" and insert -- 210°C -- therefor;
Line 65, please delete "0,25% mol" and insert -- 0.25% mol -- therefor;
Line 66, please delete "0,10% mol" and insert -- 0.10% mol --therefor;

UNITED STATES PATENT AND TRADEMARK OFFICE
CERTIFICATE OF CORRECTION

PATENT NO. : 6,180,841 B1
DATED : January 30, 2001
INVENTOR(S) : Fatutto et al.

It is certified that error appears in the above-identified patent and that said Letters Patent is hereby corrected as shown below:

Column 5,
Line 3, please delete "99,12% mol" and insert -- 99.12% mol -- therefor;
Line 4, please delete "0,40% mol" and insert -- 0.40% mol -- therefor;

Column 6,
Line 17, please delete "Selectivity of ethylene impur" and insert -- Selectivity of ethylene to impurities -- therefor;

Please delete Claim 9.

Column 4,
Lines 23, 44 & 65, please delete "EC1" and insert -- Ethylchloride -- therefor.

Column 5,
Lines 28 & 48, please delete "EC1" and insert -- Ethylchloride -- therefor.

Column 6,
Line 14, please delete "EC1" and insert -- Ethylchloride -- therefor.

Signed and Sealed this

Fourth Day of December, 2001

Attest:

*Attesting Officer*

NICHOLAS P. GODICI
*Acting Director of the United States Patent and Trademark Office*